US00PP23988P2

(12) United States Plant Patent
Bergman

(10) Patent No.: US PP23,988 P2
(45) Date of Patent: Oct. 15, 2013

(54) ***HIBISCUS* PLANT NAMED 'SAMOA WIND'**

(50) Latin Name: *Hibiscus rosa-sinensis*
Varietal Denomination: Samoa Wind

(75) Inventor: Wendy R. Bergman, Hollister, CA (US)

(73) Assignee: Aris Horticulture, Inc., Barberton, OH (US)

( * ) Notice: Subject to any disclaimer, the term of this patent is extended or adjusted under 35 U.S.C. 154(b) by 115 days.

(21) Appl. No.: 13/373,923

(22) Filed: Dec. 5, 2011

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — June Hwu
(74) *Attorney, Agent, or Firm* — C. A. Whealy

(57) ABSTRACT

A new and distinct cultivar of *Hibiscus* plant named 'Samoa Wind', characterized by its upright, somewhat outwardly spreading, uniformly mounded and dense plant habit appropriate for container production; glossy dark green-colored leaves; uniform, freely and early flowering habit; salmon pink-colored flowers; and good postproduction and garden performance.

2 Drawing Sheets

Botanical designation: *Hibiscus rosa-sinensis*.
Cultivar denomination: 'SAMOA WIND'.

BACKGROUND OF THE INVENTION

The present invention relates to a new and distinct *Hibiscus* plant, botanically known as *Hibiscus rosa-sinensis* and hereinafter referred to by the name 'Samoa Wind'.

The new *Hibiscus* plant is a product of a planned breeding program conducted by the Inventor in Alva, Fla. The objective of the breeding program is to create new freely-branching *Hibiscus* plants with a dense, uniform and compact plant habit appropriate for container production, early and uniform flowering habit, numerous flowers per lateral branch, desirable flower color and good garden performance.

The new *Hibiscus* plant originated from a cross-pollination made by the Inventor in Alva, Fla. in September, 2007 of a proprietary selection of *Hibiscus rosa-sinensis* identified as code number YB-1528, not patented, as the female, or seed, parent with a proprietary selection of *Hibiscus rosa-sinensis* identified as code number YB-2336, not patented, as the male, or pollen, parent. The new *Hibiscus* plant was discovered and selected by the Inventor as a single flowering plant within the progeny of the stated cross-pollination in a controlled greenhouse environment in Alva, Fla. on Sep. 2, 2008.

Asexual reproduction of the new *Hibiscus* plant by vegetative terminal cuttings in a controlled greenhouse environment in Alva, Fla. since February, 2009 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Samoa Wind'.

These characteristics in combination distinguish 'Samoa Wind' as a new and distinct *Hibiscus* plant:

1. Upright, somewhat outwardly spreading, uniformly mounded and dense plant habit appropriate for container production.
2. Glossy dark green-colored leaves.
3. Uniform, freely and early flowering habit.
4. Salmon pink-colored flowers.
5. Good postproduction and garden performance.

Plants of the new *Hibiscus* can be compared to plants of the female parent selection. Plants of the new *Hibiscus* differ from plants of the female parent selection in the following characteristics:

1. Plants of the new *Hibiscus* are more compact than plants of the female parent selection.
2. Plants of the new *Hibiscus* are more upright than plants of the female parent selection.
3. Flowers of plants of the new *Hibiscus* are darker pink in color than flowers of plants of the female parent selection.

Plants of the new *Hibiscus* can be compared to plants of the male parent selection. Plants of the new *Hibiscus* differ from plants of the male parent selection in the following characteristics:

1. Plants of the new *Hibiscus* are more upright than plants of the male parent selection.
2. Plants of the new *Hibiscus* and the male parent selection differ in flower color as plants of the male parent selection have orange-colored flowers with red-colored centers.

Plants of the new *Hibiscus* can be compared to plants of the *Hibiscus rosa-sinensis* 'Candy Wind', disclosed in U.S. Plant Pat. No. 11,759. In side-by-side comparisons conducted in Alva, Fla., plants of the new *Hibiscus* differed from plants of 'Candy Wind' in the following characteristics:

1. Plants of the new *Hibiscus* were more upright than plants of 'Candy Wind'.
2. Plants of the new *Hibiscus* were not as vigorous as plants of 'Candy Wind'.

3. Plants of the new *Hibiscus* had darker pink-colored flowers than plants of 'Candy Wind'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Samoa Wind' grown in a container.

The photograph on the second sheet comprises a close-up view of a typical flowering plant of 'Samoa Wind'.

DETAILED BOTANICAL DESCRIPTION

The aforementioned photographs and following observations, measurements and values describe plants grown during the summer in 15-cm containers in a fiberglass-covered greenhouse in Alva, Fla. and under environmental conditions and cultural practices which closely approximate commercial *Hibiscus* production. During the production of the plants, day temperatures ranged from 20° C. to 38° C., night temperatures ranged from 15° C. to 24° C. and light levels ranged from 3,000 to 4,000 foot-candles. Plants were pinched two times and were 23 weeks old when the photographs and the description were taken. In the description, color references are made to The Royal Horticultural Society Colour Chart, 2007 Edition, except where general terms of ordinary dictionary significance are used.

Botanical classification: *Hibiscus rosa-sinensis* 'Samoa Wind'.

Parentage:

*Female, or seed, parent*.—Proprietary selection of *Hibiscus rosa-sinensis* identified as code number YB-1528, not patented.

*Male or pollen parent*.—Proprietary selection of *Hibiscus rosa-sinensis* identified as code number YB-2336, not patented.

Propagation:

*Type*.—By vegetative terminal cuttings.

*Time to initiate roots*.—About 10 days at temperatures of 24° C.

*Time to develop roots*.—About four weeks at temperatures of 24° C.

*Root description*.—Thick, fibrous; white in color.

*Rooting habit*.—Moderate branching; moderately dense.

Plant description:

*Plant form and growth habit*.—Perennial, evergreen, upright, somewhat outwardly spreading, compact, uniformly mounded and dense; moderately vigorous growth habit.

*Branching habit*.—Freely branching habit with lateral branches potentially develop at every node; pinching enhances lateral branch development.

*Plant height*.—About 30 cm.

*Plant diameter* (*area of spread*).—About 36 cm.

Lateral branch description:

*Length*.—About 20 cm.

*Diameter*.—About 7 mm.

*Internode length*.—About 1.5 cm to 2 cm.

*Aspect*.—Upright to slightly outwardly spreading.

*Texture*.—Immature, smooth; mature, woody and rough.

*Color, immature*.—Close to 147A.

*Color, mature*.—Close to 197C.

Foliage description:

*Arrangement*.—Alternate, single; numerous; symmetrical.

*Length*.—About 8 cm.

*Width*.—About 5.5 cm.

*Shape*.—Ovate.

*Apex*.—Acute.

*Base*.—Obtuse, occasionally with cordate tendencies.

*Margin*.—Crenate.

*Texture, upper and lower surfaces*.—Smooth, glabrous.

*Luster, upper surface*.—Glossy.

*Luster, lower surface*.—Somewhat glossy.

*Venation pattern*.—Pinnate; arcuate.

*Color*.—Developing leaves, upper surface: Darker than 147A. Developing leaves, lower surface: Closest to N137B. Fully expanded leaves, upper surface: Much darker green than 147A; venation, much darker green than 147A. Fully expanded leaves, lower surface: Close to N137A; venation, close to N137A to N137B.

*Petiole*.—Length: About 3 cm. Diameter: About 5 mm. Texture, upper and lower surfaces: Slightly pubescent. Color, upper surface: Close to 147A. Color, lower surface: Close to N137B.

Flower description:

*Flower arrangement and flowering habit*.—Rounded star-shaped flowers arranged at terminal leaf axils; uniform and freely flowering habit with about five to six flowers per terminal; flowers face mostly upright to outwardly.

*Natural flowering season*.—Plants of the new *Hibiscus* flower naturally during the spring and summer or during periods of warm weather; plants flower year-round in the greenhouse.

*Flower longevity*.—Flowers last about two to three days on the plant; flowers persistent.

*Flower diameter*.—About 10 cm.

*Flower length* (*height*).—About 5.25 cm.

*Flower bud*.—Resistance to abscission during shipping: Plants of the new *Hibiscus* have been observed to resist flower bud drop when stored in a closed box for five days at 13° C. Length: About 2.4 cm. Diameter: About 1.3 cm. Shape: Ovoid. Color: Darker green than 144A.

*Petals*.—Arrangement: Corolla consists of five petals that are fused at base; petals imbricate. Length: About 6 cm. Width: About 5.6 cm. Shape: Roughly spatulate. Apex: Rounded. Base: Attenuate. Margin: Entire; slightly undulate. Texture: Smooth, glabrous; satiny; veins prominent on the lower surface. Color: When opening, upper surface: Close to 47D. When opening, lower surface: Closest to 48B to 48C. Fully opened, upper surface: Close to 47D; color does not fade with development. Fully opened, lower surface: Between 48C and 49A; color does not fade with development.

*Sepals*.—Appearance: Five sepals fused into a tubular star-shaped calyx. Length: About 2.3 cm. Width: About 1 cm. Shape: Lanceolate. Apex: Sharply acute. Margin: Entire. Texture, upper surface: Smooth, glabrous; waxy. Texture, lower surface: Slightly pubescent. Color, upper and lower surfaces: Close to 144A to more green than 144A.

*Bracts*.—Appearance: About six to seven fused at base. Length: About 1.5 cm. Width: About 5 mm. Shape: Lanceolate. Apex: Acute. Margin: Entire. Texture, upper surface: Smooth, glabrous. Texture, lower surface: Sparsely pubescent. Color, upper and lower surfaces: More green than 147A.

*Peduncles*.—Length: About 2.6 cm. Diameter: About 3.5 mm. Aspect: Upright. Strength: Strong, flexible. Texture: Smooth, glabrous. Color: More green than 146A.

*Reproductive organs*.—Androecium: Stamen number: Numerous, about 80 per flower. Filament length: About 2 mm. Filament color: Close to 47A to 47B. Anther shape: Oblong. Anther length: About 1 mm. Anther color: Close to 9A. Amount of pollen: Moderate to scarce. Pollen color: Close to 14A. Gynoecium: Pistil number: One per flower. Pistil length: About 5 cm. Style length: About 4.4 cm. Style texture: Smooth, glabrous; waxy. Style color: Towards the apex, close to 47C; towards the base, close to 45A. Stigma appearance: Five-parted, rounded. Stigma color: Close to 45A. Ovary color: Close to 157A.

*Seeds and fruits*.—Seed and fruit production has not been observed on plants of the new *Hibiscus*.

Garden performance: Plants of the new *Hibiscus* have been observed to have good garden performance and to tolerate wind, rain and temperatures ranging from about 1° C. to about 38° C.

Pathogen & pest resistance: Plants of the new *Hibiscus* grown under Florida production conditions have not been shown to be susceptible to pathogens common to *Hibiscus* such as Pseudomonas, Pythium and Phytophthora. Plants of the new *Hibiscus* have not been observed to be resistant to pests and other pathogens.

It is claimed:

1. A new and distinct *Hibiscus* plant named 'Samoa Wind' as illustrated and described.

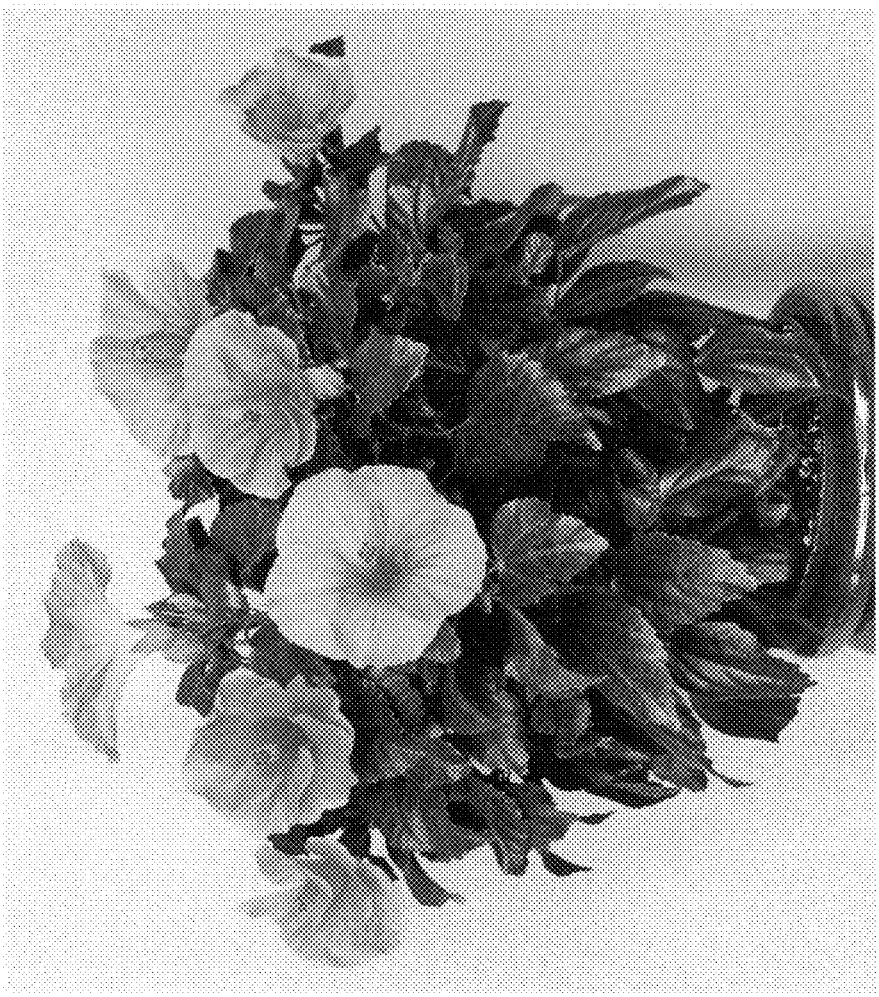

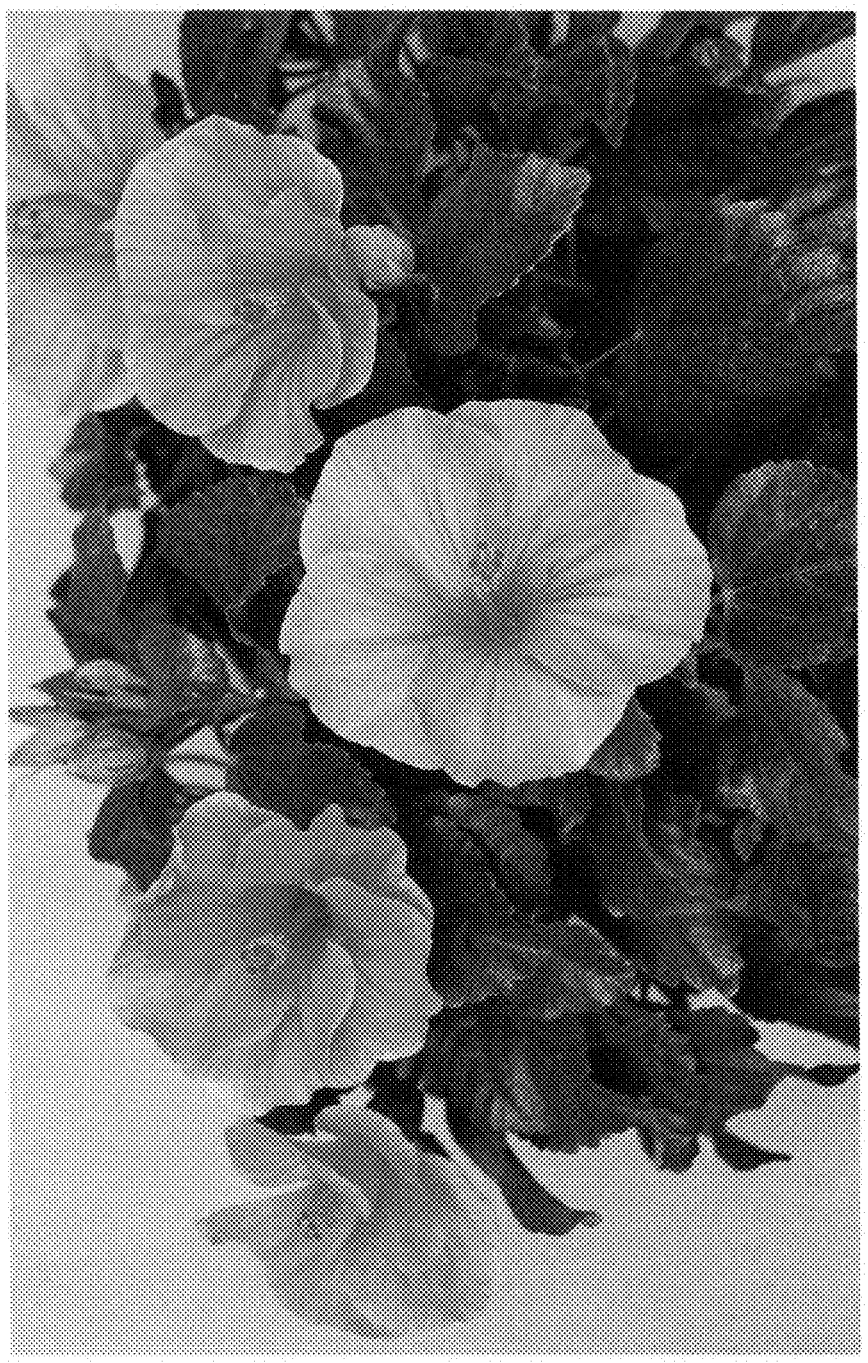

* * * * *